(12) United States Patent
Gale et al.

(10) Patent No.: US 10,682,453 B2
(45) Date of Patent: Jun. 16, 2020

(54) VASCULAR ACCESS SYSTEM WITH REINFORCEMENT MEMBER

(71) Applicant: Merit Medical Systems, Inc., South Jordan, UT (US)

(72) Inventors: David Gale, Kennesaw, GA (US); Daniel Tomko, Dallas, GA (US); Stacy Arnold, Cartersville, GA (US); Venkata Katragadda, Kennesaw, GA (US)

(73) Assignee: Merit Medical Systems, Inc., South Jordan, UT (US)

( * ) Notice: Subject to any disclaimer, the term of this patent is extended or adjusted under 35 U.S.C. 154(b) by 433 days.

(21) Appl. No.: 15/035,626

(22) PCT Filed: Nov. 11, 2014

(86) PCT No.: PCT/US2014/064968
§ 371 (c)(1),
(2) Date: May 10, 2016

(87) PCT Pub. No.: WO2015/094514
PCT Pub. Date: Jun. 25, 2015

(65) Prior Publication Data
US 2016/0279317 A1    Sep. 29, 2016

Related U.S. Application Data

(60) Provisional application No. 61/919,097, filed on Dec. 20, 2013.

(51) Int. Cl.
*A61M 1/36*       (2006.01)
*A61F 2/06*       (2013.01)

(52) U.S. Cl.
CPC ............ *A61M 1/3655* (2013.01); *A61F 2/06* (2013.01); *A61F 2220/0025* (2013.01)

(58) Field of Classification Search
CPC .. A61F 2/06; A61F 2220/0025; A61M 1/3655
See application file for complete search history.

(56) References Cited

U.S. PATENT DOCUMENTS 3,357,432 A    12/1967 Sparks
3,435,823 A    4/1969  Edwards
(Continued)

FOREIGN PATENT DOCUMENTS

DE    4418910      12/1995
DE    29515546     3/1997
(Continued)

OTHER PUBLICATIONS

International Search and the Written Opinion for PCT/US2014/064968 dated Feb. 10, 2015.
(Continued)

*Primary Examiner* — Leslie R Deak
(74) *Attorney, Agent, or Firm* — Stoel Rives LLP (57) ABSTRACT

A system for providing a continuous flow of blood between two locations in a cardiovascular system of a patient is provided. The system includes a blood conduit having a proximal portion configured to be attached to an artery. The system also includes a distal portion configured to be inserted into a blood vessel at an insertion site and to be advanced there through to a location spaced apart from the insertion site. Moreover, the system includes a reinforcement member positioned at least partially about the blood conduit in at least one of the distal portion, the proximal portion, or a combination thereof.

18 Claims, 8 Drawing Sheets

(56) References Cited

U.S. PATENT DOCUMENTS

| | | |
|---|---|---|
| 3,490,438 A | 1/1970 | Lavender et al. |
| 3,683,926 A | 8/1972 | Suzuki |
| 3,814,137 A | 6/1974 | Martinez |
| 3,818,511 A | 6/1974 | Goldberg et al. |
| 3,826,257 A | 7/1974 | Buselmeier |
| 3,853,126 A | 12/1974 | Schulte |
| 3,882,862 A | 5/1975 | Berend |
| 3,998,222 A | 12/1976 | Shihata |
| 4,076,023 A | 2/1978 | Martinez |
| 4,133,312 A | 1/1979 | Burd |
| 4,184,489 A | 1/1980 | Burd |
| 4,214,586 A | 7/1980 | Mericle |
| 4,318,401 A | 3/1982 | Zimmernan |
| 4,366,819 A | 1/1983 | Kaster |
| 4,427,219 A | 1/1984 | Madej |
| 4,441,215 A | 4/1984 | Kaster |
| 4,447,237 A | 5/1984 | Frisch et al. |
| 4,496,349 A | 1/1985 | Cosentino |
| 4,496,350 A | 1/1985 | Cosentino |
| 4,503,568 A | 3/1985 | Madras |
| 4,550,447 A | 11/1985 | Seiler, Jr. |
| 4,619,641 A | 10/1986 | Schanzer |
| 4,655,771 A | 4/1987 | Wallersten |
| 4,723,948 A | 2/1988 | Clark et al. |
| 4,734,094 A | 3/1988 | Jacob et al. |
| 4,753,236 A | 6/1988 | Healy |
| 4,771,777 A | 9/1988 | Horzewski et al. |
| 4,772,268 A | 9/1988 | Bates |
| 4,786,345 A | 11/1988 | Wood |
| 4,790,826 A | 12/1988 | Elftman |
| 4,822,341 A | 4/1989 | Colone |
| 4,848,343 A | 7/1989 | Wallsten et al. |
| 4,850,999 A | 7/1989 | Planck |
| 4,856,938 A | 8/1989 | Kuehn |
| 4,877,661 A | 10/1989 | House et al. |
| 4,898,591 A | 2/1990 | Jang et al. |
| 4,898,669 A | 2/1990 | Tesio |
| 4,917,087 A | 4/1990 | Walsh et al. |
| 4,919,127 A | 4/1990 | Pell |
| 4,929,236 A | 5/1990 | Sampson |
| 4,955,899 A | 9/1990 | Della Corna et al. |
| 5,026,513 A | 6/1991 | House et al. |
| 5,041,098 A | 8/1991 | Loiterman et al. |
| 5,042,161 A | 8/1991 | Hodge |
| 5,053,023 A | 10/1991 | Martin |
| 5,061,275 A | 10/1991 | Wallsten et al. |
| 5,061,276 A | 10/1991 | Tu et al. |
| 5,064,435 A | 11/1991 | Porter |
| 5,104,402 A | 4/1992 | Melbin |
| 5,171,227 A | 12/1992 | Twardowski et al. |
| 5,171,305 A | 12/1992 | Schickling et al. |
| 5,192,289 A | 3/1993 | Jessen |
| 5,192,310 A | 3/1993 | Herweck et al. |
| 5,197,976 A | 3/1993 | Herweck et al. |
| 5,282,860 A | 2/1994 | Matsuno et al. |
| 5,330,500 A | 7/1994 | Song |
| 5,336,616 A | 8/1994 | Livesey et al. |
| 5,399,168 A | 3/1995 | Wadsworth |
| 5,405,320 A | 4/1995 | Twardowski et al. |
| 5,405,339 A | 4/1995 | Kohnen et al. |
| 5,454,790 A | 10/1995 | Dubrul |
| 5,474,268 A | 12/1995 | Yu |
| 5,474,563 A | 12/1995 | Myler et al. |
| 5,476,451 A | 12/1995 | Ensminger et al. |
| 5,496,294 A | 3/1996 | Hergenrother et al. |
| 5,509,897 A | 4/1996 | Twardowski et al. |
| 5,558,641 A | 9/1996 | Glantz et al. |
| 5,562,617 A | 10/1996 | Finch, Jr. et al. |
| 5,562,618 A | 10/1996 | Cai et al. |
| 5,591,226 A | 1/1997 | Trerotola et al. |
| 5,607,463 A | 3/1997 | Schwartz et al. |
| 5,624,413 A | 4/1997 | Markel et al. |
| 5,637,088 A | 6/1997 | Wenner et al. |
| 5,637,102 A | 6/1997 | Tolkoff et al. |
| 5,645,532 A | 7/1997 | Horgan |
| 5,647,855 A | 7/1997 | Trooskin |
| 5,669,637 A | 9/1997 | Chitty et al. |
| 5,669,881 A | 9/1997 | Dunshee |
| 5,674,272 A | 10/1997 | Bush et al. |
| 5,676,346 A | 10/1997 | Leinsing |
| 5,743,894 A | 4/1998 | Swisher |
| 5,755,773 A | 5/1998 | Schuster |
| 5,755,775 A | 5/1998 | Trerotola et al. |
| 5,792,104 A | 8/1998 | Speckman et al. |
| 5,797,879 A | 8/1998 | Decampli |
| 5,800,512 A | 9/1998 | Lentz et al. |
| 5,800,514 A | 9/1998 | Nunez et al. |
| 5,800,522 A | 9/1998 | Campbell |
| 5,810,870 A | 9/1998 | Myers et al. |
| 5,830,224 A | 11/1998 | Cohn et al. |
| 5,840,240 A | 11/1998 | Stenoien et al. |
| 5,866,217 A | 2/1999 | Stenoien et al. |
| 5,904,967 A | 5/1999 | Ezaki et al. |
| 5,931,829 A | 8/1999 | Burbank et al. |
| 5,931,865 A | 8/1999 | Silverman et al. |
| 5,957,974 A | 9/1999 | Thompson et al. |
| 5,997,562 A | 12/1999 | Zadno-Azizi |
| 6,001,125 A | 12/1999 | Golds et al. |
| 6,019,788 A | 2/2000 | Butters et al. |
| 6,036,724 A | 3/2000 | Lentz et al. |
| 6,102,884 A | 8/2000 | Squitieri |
| 6,156,016 A | 12/2000 | Maginot |
| 6,167,765 B1 | 1/2001 | Weitzel |
| 6,171,295 B1 | 1/2001 | Garabedian |
| 6,231,085 B1 | 5/2001 | Olson |
| 6,245,098 B1 | 6/2001 | Feeser |
| 6,255,396 B1 | 7/2001 | Ding et al. |
| 6,261,255 B1 | 7/2001 | Mullis et al. |
| 6,261,257 B1 | 7/2001 | Uflacker et al. |
| 6,280,466 B1 | 8/2001 | Kugler et al. |
| 6,308,992 B1 | 10/2001 | Mitsui et al. |
| 6,309,411 B1 | 10/2001 | Lashinski et al. |
| 6,319,279 B1 | 11/2001 | Shannon et al. |
| 6,338,724 B1 | 1/2002 | Dossa |
| 6,398,764 B1 | 6/2002 | Finch, Jr. et al. |
| 6,402,767 B1 | 6/2002 | Nash et al. |
| 6,428,571 B1 | 8/2002 | Lentz et al. |
| 6,436,132 B1 | 8/2002 | Patel et al. |
| 6,582,409 B1 | 6/2003 | Squitieri |
| 6,585,762 B1 | 7/2003 | Stanish |
| 6,610,004 B2 | 8/2003 | Viole et al. |
| 6,689,096 B1 | 2/2004 | Loubens et al. |
| 6,689,157 B2 | 2/2004 | Madrid et al. |
| 6,692,461 B2 | 2/2004 | Wantink |
| 6,699,233 B2 | 3/2004 | Slanda et al. |
| 6,702,748 B1 | 3/2004 | Nita et al. |
| 6,702,781 B1 | 3/2004 | Reifart et al. |
| 6,706,025 B2 | 3/2004 | Engelson et al. |
| 6,719,781 B1 | 4/2004 | Kim |
| 6,719,783 B2 | 4/2004 | Lentz et al. |
| 6,730,096 B2 | 5/2004 | Basta |
| 6,733,459 B1 | 5/2004 | Atsumi |
| 6,740,273 B2 | 5/2004 | Lee |
| 6,749,574 B2 | 6/2004 | O'Keefe |
| 6,752,826 B2 | 6/2004 | Holloway et al. |
| 6,758,836 B2 | 7/2004 | Zawacki |
| 6,858,019 B2 | 2/2005 | McGuckin, Jr. et al. |
| 6,926,735 B2 | 8/2005 | Henderson |
| 6,976,952 B1 | 12/2005 | Maini et al. |
| 6,981,987 B2 | 1/2006 | Huxel et al. |
| 7,011,645 B2 | 3/2006 | McGuckin, Jr. et al. |
| 7,025,741 B2 | 4/2006 | Cull |
| 7,036,599 B2 | 5/2006 | Matteucci |
| 7,101,356 B2 | 9/2006 | Miller |
| 7,131,959 B2 | 11/2006 | Blatter |
| 7,211,074 B2 | 5/2007 | Sansoucy |
| 7,244,271 B2 | 7/2007 | Lenz et al. |
| 7,244,272 B2 | 7/2007 | Dubson et al. |
| 7,252,649 B2 | 8/2007 | Sherry |
| 7,297,158 B2 | 11/2007 | Jensen |
| 7,399,296 B2 | 7/2008 | Poole et al. |
| 7,438,699 B2 | 10/2008 | Pecor et al. |
| 7,452,374 B2 | 11/2008 | Hain et al. |
| 7,507,229 B2 | 3/2009 | Hewitt et al. |

(56) References Cited

U.S. PATENT DOCUMENTS

| | | |
|---|---|---|
| 7,588,551 B2 | 9/2009 | Gertner |
| 7,708,722 B2 | 5/2010 | Glenn |
| 7,722,665 B2 | 5/2010 | Anwar et al. |
| RE41,448 E | 7/2010 | Squitieri |
| 7,762,977 B2 | 7/2010 | Porter et al. |
| 7,789,908 B2 | 9/2010 | Sowinski et al. |
| 7,828,833 B2 | 11/2010 | Haverkost et al. |
| 7,833,214 B2 | 11/2010 | Wilson et al. |
| 7,846,139 B2 | 12/2010 | Zinn et al. |
| 7,850,675 B2 * | 12/2010 | Bell ............... A61M 25/0045 604/523 |
| 7,850,705 B2 | 12/2010 | Bachinski et al. |
| 7,922,757 B2 | 4/2011 | McGuckin |
| 7,972,314 B2 | 7/2011 | Bizup et al. |
| 8,079,973 B2 | 12/2011 | Herrig et al. |
| 8,092,435 B2 | 1/2012 | Beling et al. |
| 8,097,311 B2 | 1/2012 | Wang et al. |
| 8,313,524 B2 | 11/2012 | Edwin et al. |
| 8,512,312 B2 | 8/2013 | Sage |
| 8,690,815 B2 | 4/2014 | Porter et al. |
| 2001/0053930 A1 | 12/2001 | Kugler et al. |
| 2002/0049403 A1 | 4/2002 | Alanis |
| 2002/0055766 A1 | 5/2002 | Wallace et al. |
| 2002/0055771 A1 | 5/2002 | Sandock |
| 2002/0099432 A1 | 7/2002 | Yee |
| 2002/0151761 A1 | 10/2002 | Viole et al. |
| 2003/0100859 A1 | 5/2003 | Henderson et al. |
| 2003/0135258 A1 | 7/2003 | Andreas et al. |
| 2003/0135261 A1 | 7/2003 | Kugler et al. |
| 2003/0139806 A1 | 7/2003 | Haverkost et al. |
| 2003/0181969 A1 | 9/2003 | Kugler et al. |
| 2003/0212385 A1 | 11/2003 | Brenner et al. |
| 2003/0212431 A1 | 11/2003 | Brady et al. |
| 2004/0024442 A1 | 2/2004 | Sowinkski et al. |
| 2004/0073282 A1 | 4/2004 | Stanish |
| 2004/0078071 A1 | 4/2004 | Escamilla et al. |
| 2004/0099395 A1 | 5/2004 | Wang et al. |
| 2004/0147866 A1 | 7/2004 | Blatter et al. |
| 2004/0193242 A1 | 9/2004 | Lentz et al. |
| 2004/0215337 A1 | 10/2004 | Hain et al. |
| 2004/0236412 A1 | 11/2004 | Brar |
| 2005/0004553 A1 | 1/2005 | Douk |
| 2005/0137614 A1 | 6/2005 | Porter et al. |
| 2005/0192559 A1 | 9/2005 | Michels et al. |
| 2005/0203457 A1 | 9/2005 | Smego |
| 2005/0209581 A1 | 9/2005 | Butts et al. |
| 2005/0215938 A1 | 9/2005 | Khan et al. |
| 2006/0058867 A1 | 3/2006 | Thistle et al. |
| 2006/0064159 A1 | 3/2006 | Porter et al. |
| 2006/0081260 A1 | 4/2006 | Eells et al. |
| 2006/0118236 A1 | 6/2006 | House et al. |
| 2007/0078412 A1 | 4/2007 | McGuckin, Jr. et al. |
| 2007/0078416 A1 | 4/2007 | Eliasen |
| 2007/0078438 A1 | 4/2007 | Okada |
| 2007/0088336 A1 | 4/2007 | Dalton |
| 2007/0123811 A1 | 5/2007 | Squitieri |
| 2007/0135775 A1 | 6/2007 | Edoga et al. |
| 2007/0142850 A1 | 6/2007 | Fowler |
| 2007/0161958 A1 | 7/2007 | Glenn |
| 2007/0167901 A1 | 7/2007 | Herrig et al. |
| 2007/0168019 A1 | 7/2007 | Amplatz et al. |
| 2007/0173868 A1 | 7/2007 | Bachinski et al. |
| 2007/0191779 A1 | 8/2007 | Shubayev et al. |
| 2007/0197856 A1 | 8/2007 | Gellman et al. |
| 2007/0213838 A1 | 9/2007 | Hengelmolen |
| 2007/0219510 A1 | 9/2007 | Zinn et al. |
| 2007/0233018 A1 | 10/2007 | Bizup et al. |
| 2007/0249986 A1 | 10/2007 | Smego |
| 2007/0249987 A1 | 10/2007 | Gertner |
| 2007/0265584 A1 | 11/2007 | Hickman et al. |
| 2007/0293823 A1 | 12/2007 | Sherry |
| 2007/0293829 A1 | 12/2007 | Conlon et al. |
| 2008/0009781 A1 | 1/2008 | Anwar et al. |
| 2008/0027534 A1 | 1/2008 | Edwin et al. |
| 2008/0167595 A1 | 7/2008 | Porter et al. |
| 2008/0221469 A1 | 9/2008 | Shevchuk |
| 2008/0306580 A1 | 12/2008 | Jenson et al. |
| 2009/0076587 A1 | 3/2009 | Cully et al. |
| 2009/0137944 A1 | 5/2009 | Haarala et al. |
| 2009/0227932 A1 | 9/2009 | Herrig |
| 2009/0234267 A1 | 9/2009 | Ross |
| 2009/0318895 A1 | 12/2009 | Lachner |
| 2010/0160847 A1 | 6/2010 | Braido et al. |
| 2010/0161040 A1 | 6/2010 | Braido et al. |
| 2010/0198079 A1 | 8/2010 | Ross |
| 2010/0268188 A1 | 10/2010 | Hanson |
| 2010/0268196 A1 | 10/2010 | Hastings et al. |
| 2011/0015723 A1 | 1/2011 | Batiste et al. |
| 2011/0054312 A1 | 3/2011 | Bell et al. |
| 2011/0112482 A1 | 5/2011 | Redd |
| 2011/0208218 A1 | 8/2011 | Ball |
| 2011/0257609 A1 | 10/2011 | Bizup et al. |
| 2011/0264080 A1 | 10/2011 | Lim et al. |
| 2011/0295181 A1 | 12/2011 | Dann et al. |
| 2012/0059305 A1 | 3/2012 | Akingba |
| 2012/0065652 A1 | 3/2012 | Cully et al. |
| 2012/0078202 A1 | 3/2012 | Beling et al. |
| 2013/0060268 A1 | 3/2013 | Herrig |
| 2013/0338559 A1 | 12/2013 | Franano et al. |
| 2014/0018721 A1 | 1/2014 | Gage et al. |
| 2014/0192567 A1 | 7/2014 | Balocco |
| 2014/0276215 A1 | 9/2014 | Nelson |
| 2014/0288638 A1 | 9/2014 | Knight et al. |
| 2015/0051532 A1 | 2/2015 | Tomko et al. |
| 2016/0129177 A1 | 5/2016 | Herrig |

FOREIGN PATENT DOCUMENTS

| | | |
|---|---|---|
| DE | 102008055587 | 8/2009 |
| EP | 0540834 | 5/1993 |
| EP | 1797831 | 6/2007 |
| JP | 5714358 | 1/1982 |
| JP | 62112567 | 5/1987 |
| JP | 04507050 | 12/1992 |
| JP | 05212107 | 8/1993 |
| JP | 06105798 | 4/1994 |
| JP | 0984871 | 3/1997 |
| JP | 09264468 | 7/1997 |
| JP | 2003501223 | 1/2003 |
| JP | 2008511414 | 4/2008 |
| WO | 198403036 | 8/1984 |
| WO | 1990085509 | 8/1990 |
| WO | 199519200 | 7/1995 |
| WO | 199624399 | 8/1996 |
| WO | 1998034676 | 8/1998 |
| WO | 2000027299 | 5/2000 |
| WO | 200076577 | 12/2000 |
| WO | 200105447 | 1/2001 |
| WO | 200105463 | 1/2001 |
| WO | 2001005463 | 1/2001 |
| WO | 2001028456 | 4/2001 |
| WO | 2004032991 | 4/2004 |
| WO | 2004112880 | 12/2004 |
| WO | 2006026687 | 9/2006 |
| WO | 2009059371 | 5/2009 |
| WO | 2010059102 | 5/2010 |
| WO | 2011060386 | 5/2011 |
| WO | 2011153302 | 12/2011 |

OTHER PUBLICATIONS

European Search Report dated Jun. 8, 2005 for EP05006233.0.
European Search Report dated Dec. 3, 2013 for EP05793066.1.
International Preliminary Report dated Mar. 12, 2014 for PCT/US2012/053967.
International Search Report and Written Opinion dated Jan. 28, 2015 for PCT/US2014/049547.
International Search Report and Written Opinion dated Mar. 15, 2013 for PCT/US2012/053967.
International Search Report and Written Opinion dated May 3, 2013 for PCT/US2012/053967.
International Search Report and Written Opinion dated May 6, 1998 for PCT/US1998/001939.

(56) References Cited

OTHER PUBLICATIONS

International Search Report and Written Opinion dated Jun. 3, 2009 for PCT/US2009/035923.
International Search Report and Written Opinion dated Jun. 20, 2007 for PCT/US2006/044564.
Notice of Allowance dated Mar. 15, 2010 for U.S. Appl. No. 11/216,536.
Notice of Allowance dated Oct. 4, 2013 for U.S. Appl. No. 12/831,092.
Office Action dated Jan. 9, 2018 for U.S. Appl. No. 14/450,468.
Office Action dated Feb. 6, 2013 for U.S. Appl. No. 12/831,092.
Office Action dated Feb. 21, 2017 for U.S. Appl. No. 14/192,567.
Office Action dated May 5, 2010 for U.S. Appl. No. 10/962,200.
Office Action dated Jun. 9, 2016 for U.S. Appl. No. 14/192,567.
Office Action dated Jun. 15, 2017 for U.S. Appl. No. 14/192,567.
Office Action dated Aug. 7, 2017 for U.S. Appl. No. 14/450,468.
Office Action dated Aug. 12, 2010 for U.S. Appl. No. 10/962,200.
Office Action dated Aug. 15, 2016 for U.S. Appl. No. 14/332,091.
Office Action dated Sep. 20, 2012 for U.S. Appl. No. 12/831,092.
Office Action dated Oct. 27, 2015 for U.S. Appl. No. 14/192,567.
Office Action dated Nov. 26, 2007 for U.S. Appl. No. 10/962,200.
Office Action dated Dec. 5, 2017 for U.S. Appl. No. 14/995,270.
Office Action dated Dec. 20, 2017 for U.S. Appl. No. 14/192,567.
Office Action dated Dec. 30, 2016 for U.S. Appl. No. 14/450,468.
Clinical Reveiw of MTI, Onxy Liquid Embolization System, available at http://www.fda.gov/ohrms/dockets/ac/03/briefing/3975b1-02-clinical-review.pdf. accessed Aug. 29, 2005.
Besarab, et al.,Measuring the Adequacy of Hemodialysis Access, Current Opinion in Nephrology and Hypertension, Rapid Science Publishers ISSN ,1996 ,1062-4821.
Coulson MD, et al.,Modification of Venous End of Dialysis Grafts: An Attempt to Reduce Neointimal Hyperplasia, Dialysis & Transplantation, vol. 29 No. 1 ,Jan. 2000 ,10-18.
Coulson MD, Phd, et al.,A Combination of the Elephant Trunk Anastomosis Technique and Vascular Clips for Dialysis Grafts, Surgical Rounds ,Nov. 1999 ,596-608.
Kanterman, et al.,Dialysis Access Grafts: Anatomic Location of Venous Stenosis and Results of Angioplasty, Interventional Radiology, vol. 195 No. 1, 195 ,Apr. 1995 ,135-139.
Kumpe, et al.,Angioplasty/Thrombolytic Treatment of Failing and Failed Hemodialysis Access Sites: Comparison with Surgical Treatment, Progress in Cardiovascular Diseases, vol. XXXIV No. 4 ,Jan./Feb. 1992 ,263-278.
Lin, et al.,Contemporary Vascular Access Surgery for Chronic Haemodialysis, They Royal College of Surgeons of Edinburgh, J.R. Coll, Surg, Edinb., 41 ,Jun. 1996 ,164-169.
Peterson, et al.,Subclavian Venous Stenosis: A Complication of Subclavian Dialysis, The Journal of American Medical Association, vol. 252 No. 24 ,Dec. 28, 1994 ,3404-3406.
Raju M.D., et al.,Techniques for Insertion and Management of Complications, PTFE Grafts for Hemodialysis Access, Ann. Surg., vol. 206 No. 5 ,Nov. 1987 ,666-673.
Sharafuddin, et al.,Percutaneous Balloon-Assisted Aspiration Thrombectomy of clotted ahemodialysis Access Grafts, Journal of Vascular and Interventional Radiology, vol. 7 No. 2 ,Mar.-Apr. 1996 ,177-183.
Office Action dated Apr. 16, 2020 for U.S. Appl. No. 15/868,313.

\* cited by examiner

VASCULAR ACCESS SYSTEM WITH REINFORCEMENT MEMBER

CROSS REFERENCE TO RELATED APPLICATION

The present disclosure claims priority to and the benefit of U.S. provisional patent application No. 61/919,097, filed on 20 Dec. 2013, which is incorporated by reference herein in its entirety.

FIELD

The present disclosure relates to a fluid-carrying conduit, such as an implantable vascular conduit, comprising one or more reinforcement members.

BACKGROUND

In the United States, approximately 400,000 people have end-stage renal disease requiring chronic hemodialysis. Permanent vascular access sites for performing hemodialysis may be formed by creating an arteriovenous (AV) anastomosis whereby a vein is attached to an artery to form a high-flow shunt or fistula. A vein may be directly attached to an artery, but it may take 6 to 8 weeks before the venous section of the fistula has sufficiently matured to provide adequate blood flow for use with hemodialysis. Moreover, a direct anastomosis may not be feasible in all patients due to anatomical considerations.

Other patients may require the use of artificial graft material to provide an access site between the arterial and venous vascular systems. Patency rates of grafts are still not satisfactory, as the overall graft failure rate remains high. Temporary catheter access is also an option. However, the use of temporary catheter access exposes the patient to an additional risk of bleeding and infection, as well as discomfort.

Vascular access systems are known in the art. For example, U.S. Pat. No. 6,102,884 to Squitieri, U.S. Pat. No. 7,762,977 to Porter, and U.S. Pat. No. 8,079,973 to Harrig et al. describe implantable blood conduit systems which include (i) an extravascular blood conduit that has a proximal end adapted to couple with a first vascular segment of a patient and a distal end adapted to be inserted into a second vascular segment of the patient; (ii) a catheter having a proximal portion and a distal portion that, when implanted, floats freely within the second vascular segment; and (iii) a connector for fluidly coupling the proximal end of the blood conduit with the catheter with the proximal portion. It would be desirable to provide improved and/or alternative conduits or catheters that eliminate or at least minimize kinking, compression, or other obstructions.

SUMMARY

Some or all of the above needs and/or problems may be addressed by certain embodiments disclosed herein. For example, in certain embodiments, a system for providing a continuous flow of blood between two locations in a cardiovascular system of a patient is provided. The system includes a blood conduit having a proximal portion configured to be attached to an artery. The system also includes a distal portion configured to be inserted into a blood vessel at an insertion site and to be advanced therethrough to a location spaced apart from the insertion site. Moreover, the system includes a reinforcement member positioned at least partially about the blood conduit in at least one of the distal portion, the proximal portion, or a combination thereof.

Other embodiments, aspects, and features of the disclosure will become apparent to those skilled in the art from the following detailed description, the accompanying drawings, and the appended claims.

BRIEF DESCRIPTION OF THE DRAWINGS

The structure and method of using the devices, systems, and methods described herein will be better understood with the following detailed description of embodiments, along with the accompanying illustrations, which are not necessarily drawn to scale.

DETAILED DESCRIPTION

Improved hemodialysis and vascular access systems and methods have been developed. In a broad sense, certain embodiments include systems and methods for providing one or more fluid-carrying conduits, such as an implantable vascular conduit. The fluid-carrying conduits may be arteriovenous (AV) shunts or catheters in various embodiments. For example, the embodiments described herein may improve flow between points in a patient's vasculature. In some instances, the vascular access system described herein may include a first portion of a blood-carrying conduit configured for use as an inflow component and a second portion of the blood-carrying conduit configured for use as an outflow component. Techniques for reinforcing the inflow and outflow components are provided.

In certain embodiments, the techniques for reinforcing the inflow and outflow components improve over, and/or build upon, the techniques described in U.S. Pat. Nos. 8,079,973, 8,534,033, and U.S. Application Publication No. 2013/0060268, which are all hereby incorporated by reference in their entirety.

The inflow component can be any of a variety of blood conduits that are able to receive blood into the vascular access system from the patient's vasculature. Such blood conduits can have a construction similar to a vascular graft made of ePTFE (expanded polytetrafluoroethylene), Dacron, or other suitable materials. Any suitable graft material may be used. Other suitable materials can include a material that is biocompatible with an artery and is non-thrombogenic or minimally thrombogenic. The inflow component may be adapted for attachment to an artery. For example, the inflow component may be attached to a brachial artery by an end-to-side anastomosis. In some instances, the inflow component preferably is adapted for long-term attachment to an artery, although short-term applications may also be implemented.

In a preferred embodiment, the inflow component includes a region suitable for repeated needle access. For example, a length of the inflow component can be configured to be pierced by a needle to enable blood to be withdrawn from and returned to the system, e.g., for hemodialysis.

The outflow component can be any of a variety of blood conduits that are able to return blood from the vascular access system to a patient's vascular system. In some instances, the outflow component includes a catheter for returning blood to the patient's vasculature. As used herein, "catheter" is a broad term that includes any blood-carrying conduit that can be at least partially inserted into a blood vessel and advanced therein to a selected location, including into the atrium or elsewhere. In some instances, the outflow component is attached by an end-to-side anastomosis to a vein. In other instances, the outflow component extends into a vein or into the central venous system. In certain embodiments, the outflow component is adapted such that at least a distal end portion thereof can freely float within a vascular segment when the vascular access system is applied to a patient. The inflow component and the outflow component may be made of the same material or different materials.

Figure 1:
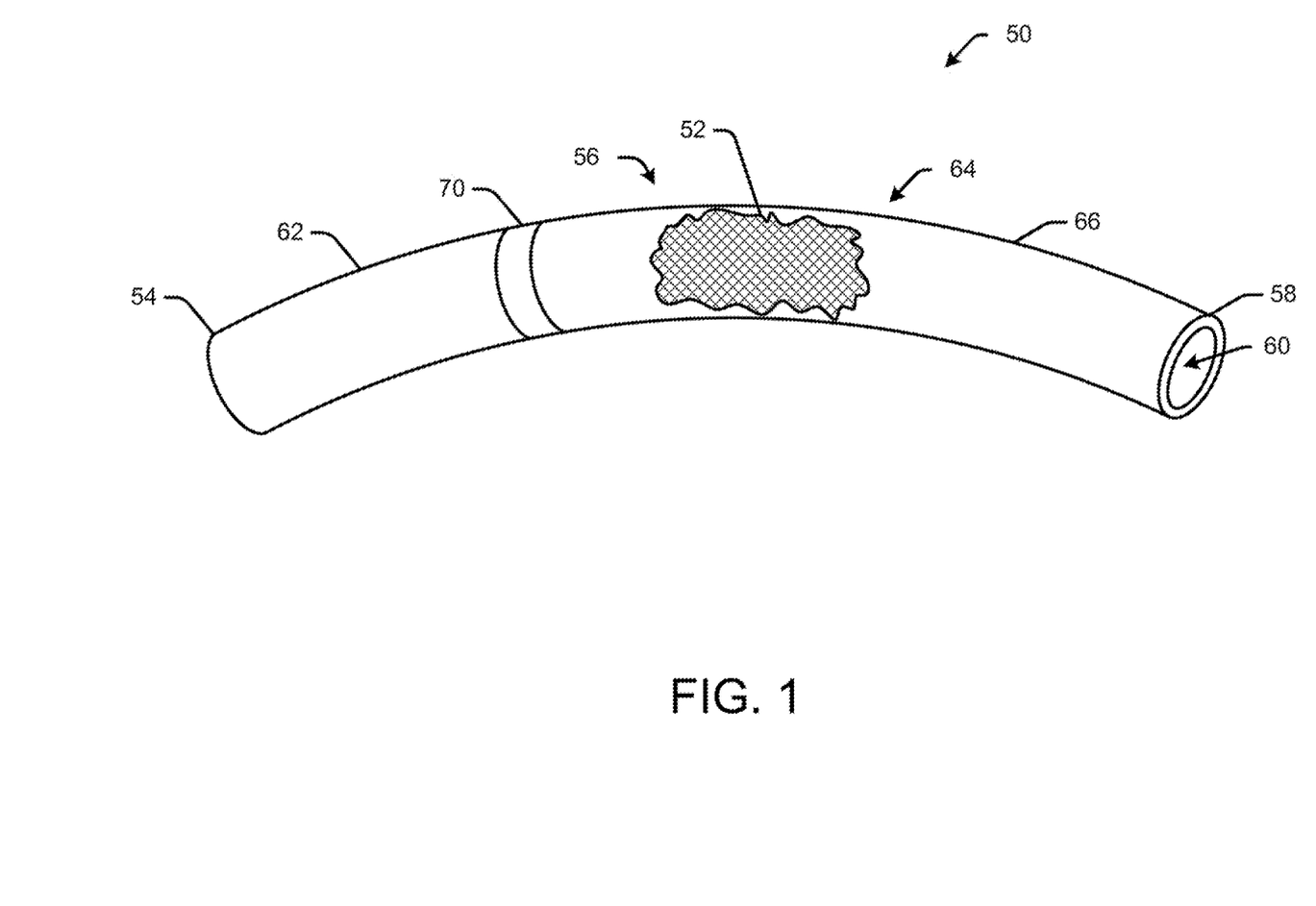
FIG. 1 schematically depicts an example embodiment of a vascular access system.

FIG. 1 illustrates one embodiment of a vascular access system 50 having a plurality of components assembled together to define a lumen 60. The lumen 60 provides a blood conduit or pathway configured to shunt blood from a first vascular segment to a second vascular segment. The vascular access system 50 has a proximal end 54 and a distal end 58 and a lumen 60 that extends between the proximal end 54 and the distal end 58. In some embodiments, the proximal end 54 is adapted to couple with (e.g., attached to) a first vascular segment, and the distal end 58 can be adapted to be coupled with (e.g., inserted into) a second vascular segment. The lumen 60 preferably extends between the proximal end 54 and the distal end 58. The lumen 60 can also be accessed from outside the patient to facilitate dialysis or other treatment.

In certain embodiments, as illustrated in FIG. 1, the vascular access system 50 includes a connector 70 adapted to fluidly connect a first conduit 62, such as an inflow component or graft, and a second conduit 66, such as an outflow component or catheter, to form the lumen 60. In certain embodiments, the first conduit 62 extends from the proximal end 54 toward the distal end 58, and the second conduit extends from the distal end 58 toward the proximal end 54. The connector 70 can be positioned between the first conduit 62 and the second conduit 66 such that a distal portion of the first conduit 62 is configured to be connected to a proximal portion of the connector 70, and a proximal portion of the second conduit 66 is configured to be connected to a distal portion of the connector 70. The connector 70 and/or the first conduit 62 and/or the second conduit 66 can be provided and/or integrated with one or more connecting devices to connect or enhance the security of the connection between the first conduit 62 and the second conduit 66. In some instances, the connector 70 is omitted, and the first conduit 62 and the second conduit 66 are integral. That is, the first conduit 62 and the second conduit 66 may be a single piece.

In certain embodiments, the wall defining the lumen 60 includes a reinforcement member 52. The reinforcement member 52 may comprise a braided structure, a woven structure, an intra-luminal stent-type structure, a coil structure, a laser cut tube structure, a linked reinforcement tube structure, a series of interconnected hard segments, a corrugated tube structure, axial projections, radial projections, axial or radial channels, or the like. The reinforcement member 52 may be any suitable structure. IThe reinforcement member 52 generally is biocompatible. The reinforcement member 52 may be formed of nitinol or another nickel titanium alloy, cobalt chrome, polyether ether ketone (PEEK) or another thermoplastic polymer, a ceramic, silicone, or another suitable material or composite thereof. The reinforcement member 52 may be made of or coated with any suitable biocompatible material. FIG. 1 depicts the reinforcement member 52 partially (in a partial cutaway view) for clarity.

The reinforcement member 52 can extend to the proximal end 54 and/or toward the distal end 58 of the lumen 60. That is, the first conduit 62, the second conduit 66, or a combination thereof may include the reinforcement member 52. In some instances, the first conduit 62 includes the reinforcement member 52 and the second conduit 66 does not include a reinforcement member, or vice versa. In some instances, the reinforcement member 52 is configured to at least partially resist radial compression of the lumen 60. Also, the reinforcement member 52 can be configured to at least partially provide resistance to kinking of the lumen 60. In this manner, the reinforcement member 52 may ensure that fluid is able to flow through the lumen 60 unobstructed or with minimal obstruction.

In certain embodiments, the reinforcement member 52 includes a proximal end 56 and a distal end 64. The reinforcement member 52 can extend along the lumen 60 such that the proximal end 56 of the reinforcement member 52 extends to or beyond the proximal end 54 of the lumen 60. Similarly, the reinforcement member 52 can extend along the lumen 60 such that the distal end 64 of the reinforcement member 52 extends to or beyond the distal end 58 of the lumen 60. The reinforcement member 52 may be positioned at any location between or beyond the proximal end 54 of the lumen 60 and/or the distal end 58 of the lumen 60.

The reinforcement member 52 can be disposed, partially or completely, about the circumference of the lumen 60. For example, certain segments of the lumen 60 may be completely surrounded by the reinforcement member 52, while other segments of the lumen 60 may be partially surrounded by the reinforcement member 52. In other instances, certain portions of the lumen 60 may not include the reinforcement member 52.

Figure 2:
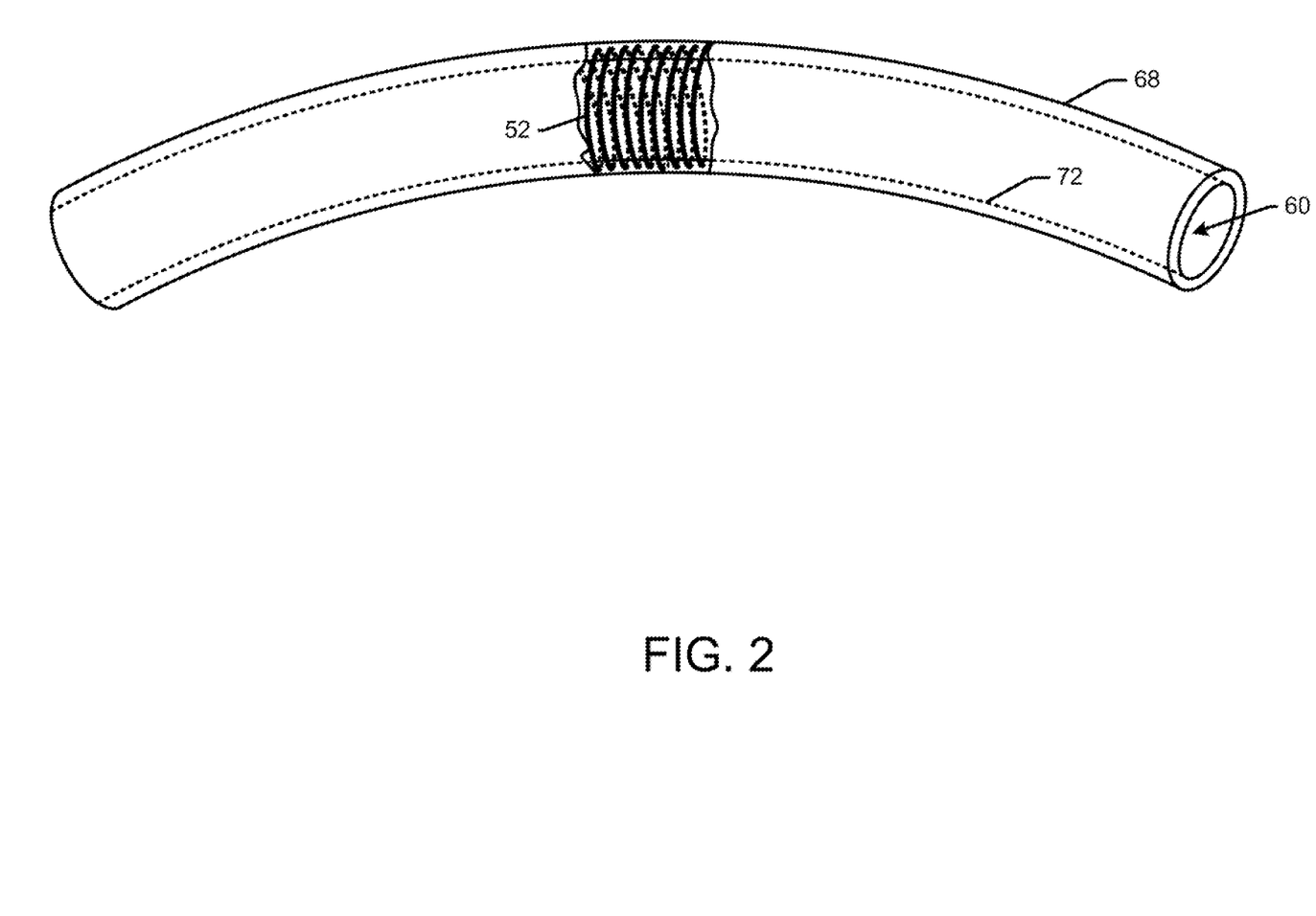
FIG. 2 schematically depicts an example embodiment of a vascular access system.

FIG. 2 depicts the reinforcement member 52 embedded within the wall defining the lumen 60. In one embodiment, the reinforcement member 52 is embedded in the wall defining the lumen 60 such that an outer surface 68 of the wall defining the lumen 60 surrounds the reinforcement member 52. In some instances, the reinforcement member 52 is disposed radially outward of an inner surface 72 of the wall defining the lumen 60. In this manner, in certain embodiments, the reinforcement member 52 is disposed between the inner surface 72 and the outer surface 68 of the wall defining the lumen 60. In some instances, the reinforcement member 52 is disposed within the wall defining the lumen 60 such that the outer surface 68 and/or the inner surface 72 of the wall defining the lumen 60 are substantially smooth.

Figure 3:
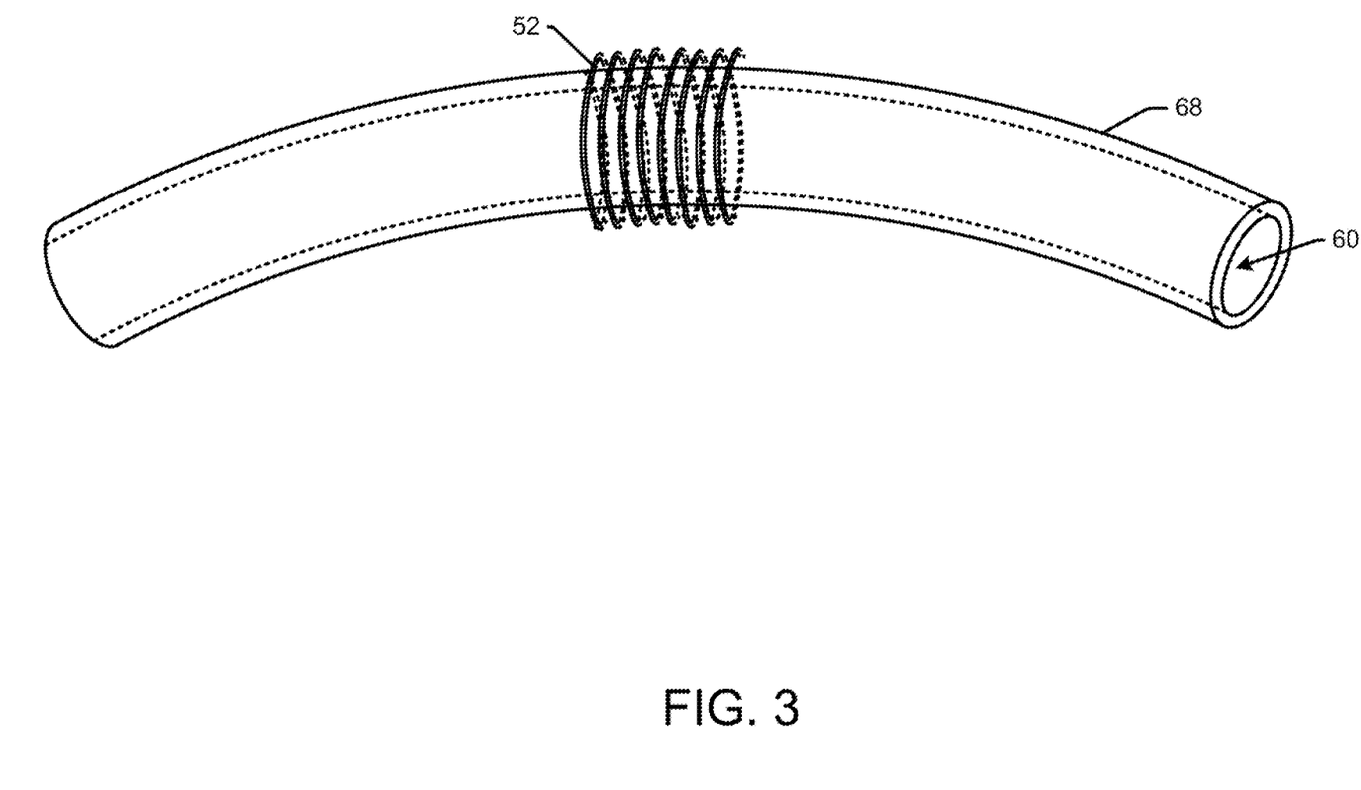
FIG. 3 schematically depicts an example embodiment of a vascular access system.

In other instances, as depicted in FIG. 3, the reinforcement member 52 is disposed on or about the outer surface 68 of the wall defining the lumen 60. For example, the reinforcement member 52 may surround, project or protrude from the outer surface 68 of the wall defining the lumen 60.

In some instances, the reinforcement member 52 may be coated with a protective layer of material.

Figure 4:
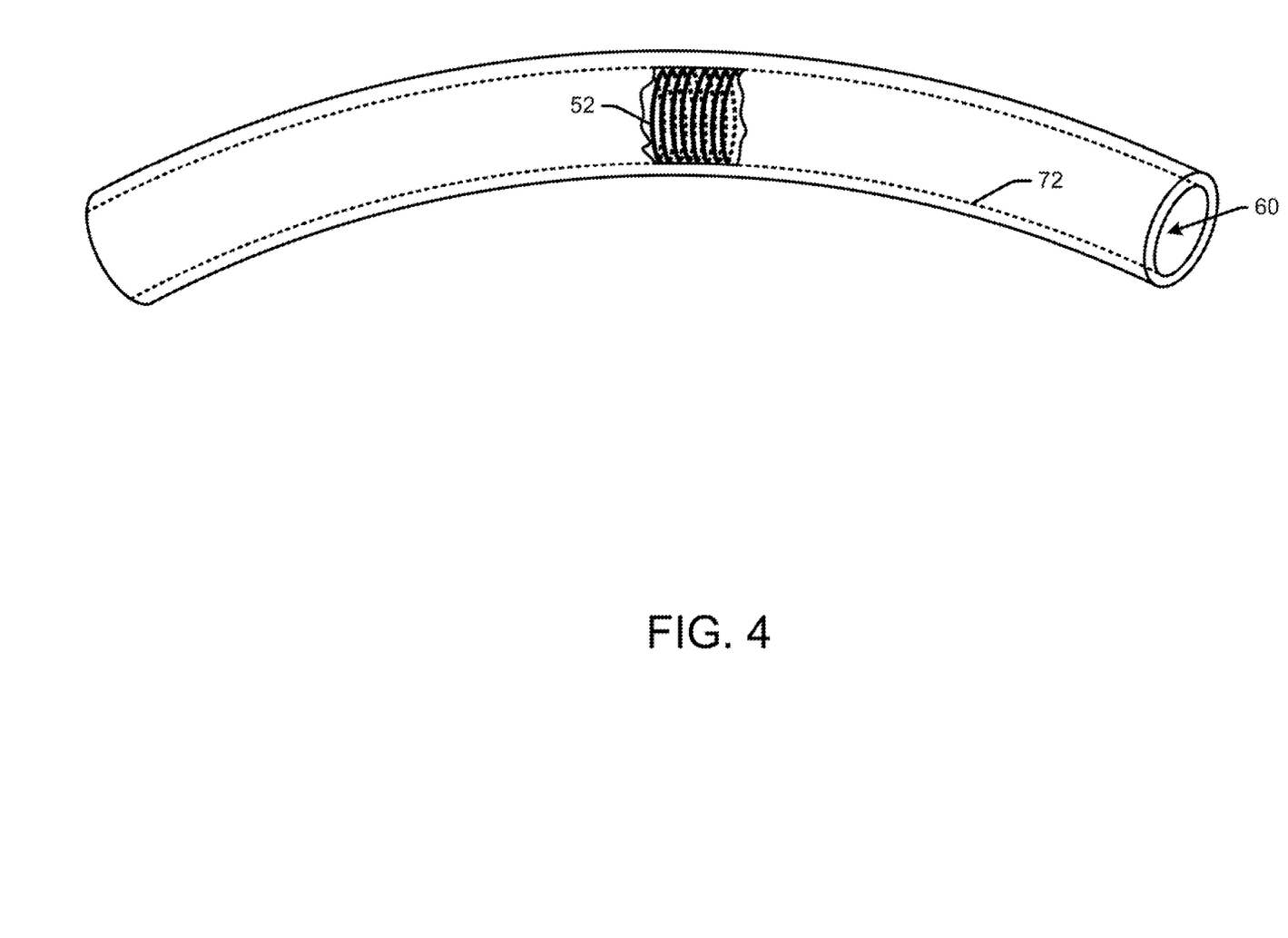
FIG. 4 schematically depicts an example embodiment of a vascular access system.

In yet other instances, as depicted in FIG. 4, the reinforcement member 52 is disposed radially inward of the inner surface 72 of the wall defining the lumen 60. For example, the reinforcement member 52 may be positioned about or protrude inward from the inner surface 72 of the wall defining the lumen 60. The reinforcement member 52 may be configured to prevent or substantially minimize kinking, crushing, and/or other phenomena that can cause at least partial collapse of the lumen 60. In this manner, fluid flow within the lumen 60 is unobstructed or at least substantially unobstructed. In some instances, the reinforcement member 52 is coated with a protective layer of material so as to provide a smooth inner surface of the wall(s) defining lumen 60.

Figure 5:
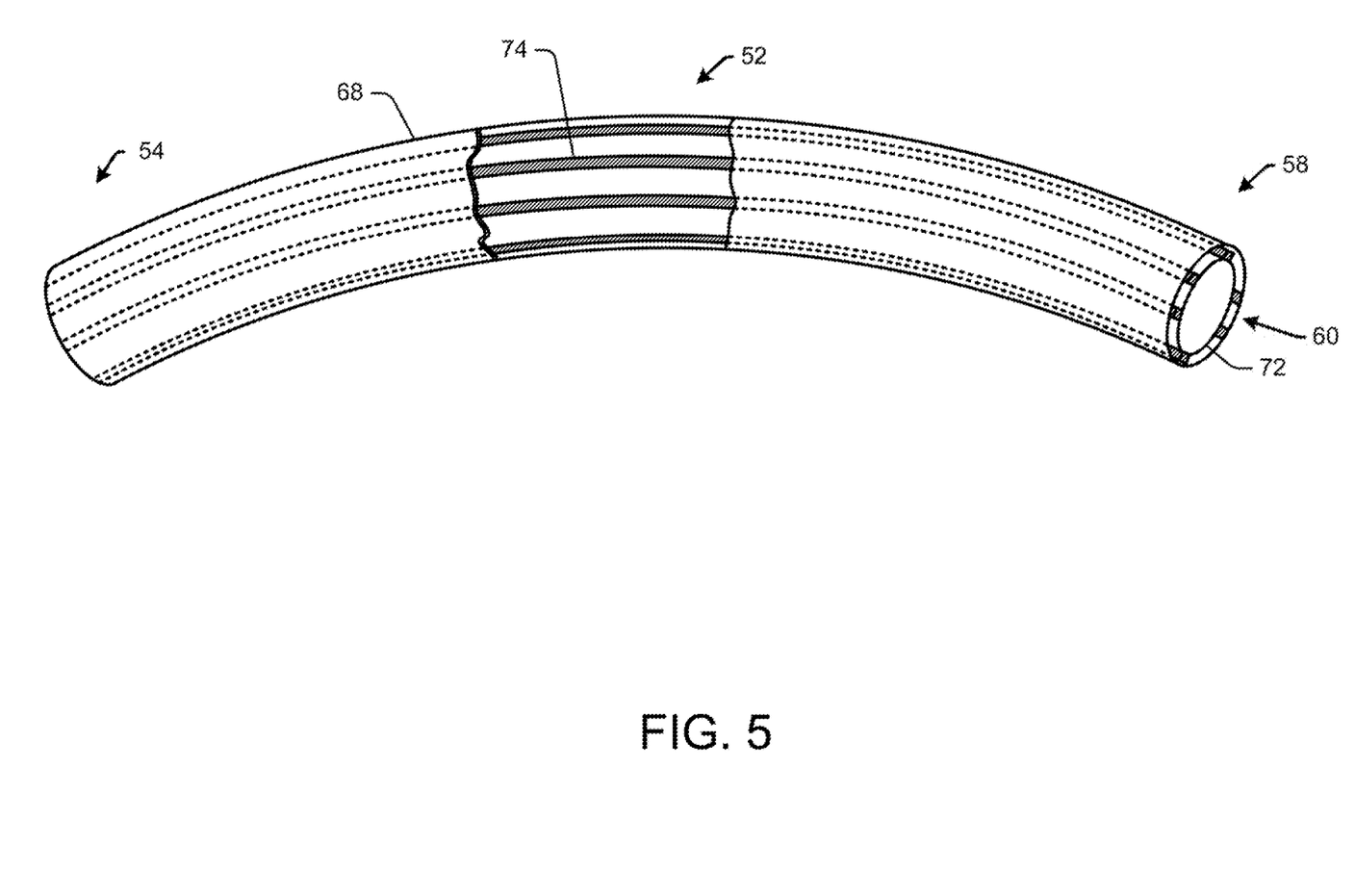
FIG. 5 schematically depicts an example embodiment of a vascular access system.

As noted above, in certain embodiments, the reinforcement member 52 is an axial projection. That is, the reinforcement member may be elongated and extend about the lumen 60 and in a direction substantially parallel to the lumen 60. For example, as depicted in FIG. 5, the reinforcement member 52 includes one or more axial projections 74 extending from the proximal end 54 of the lumen 60 to the distal end of the lumen 60 or anywhere therebetween. In some instances, the axial projections 74 extend beyond the proximal end 54 of the lumen 60 and/or the distal end 58 of the lumen 60. In other instances, the axial projections 74 are located at any point between the proximal end 54 of the lumen 60 and the distal end 58 of the lumen 60. The axial projections 74 may comprise elongated protrusions, ribs, struts, etc., or the like oriented in and/or on the wall defining the lumen 60, along the length of the lumen 60. In some instances, the axial projections 74 are positioned between the inner surface 72 and the outer surface 68 of the wall defining the lumen 60. In other instances, the axial projections 74 extend radially outward from the outer surface 68 of the wall defining the lumen 60. For example, the axial projections 74 may be extruded from the outer surface 68 of the wall defining the lumen 60. In yet other instances, the axial projections 74 extend radially inward from the inner surface 72 of the wall defining the lumen 60. The axial projections 74 may be spaced apart from one another about the circumference of the lumen 60. Any number of axial projections 74 may be used. In embodiments, a device may have as few as 1, 2, 3, 4, 5, 6, 7, 8, 9, 10, or 12 axial projections, as many as 20, 30, 40, 50, 60, 80, or 100 axial projections, or a number of axial projections within a range of any combination of these numbers.

In certain embodiments, the axial projections 74 are substantially linear. In other embodiments, the axial projections 74 are curved. For example, the axial projections 74 may form a spiral about the lumen 60. In another example, the axial projections 74 may each be curved in a wave-like configuration about the lumen 60. The axial projections 74 may be any shape or combination of shapes.

Figure 6:
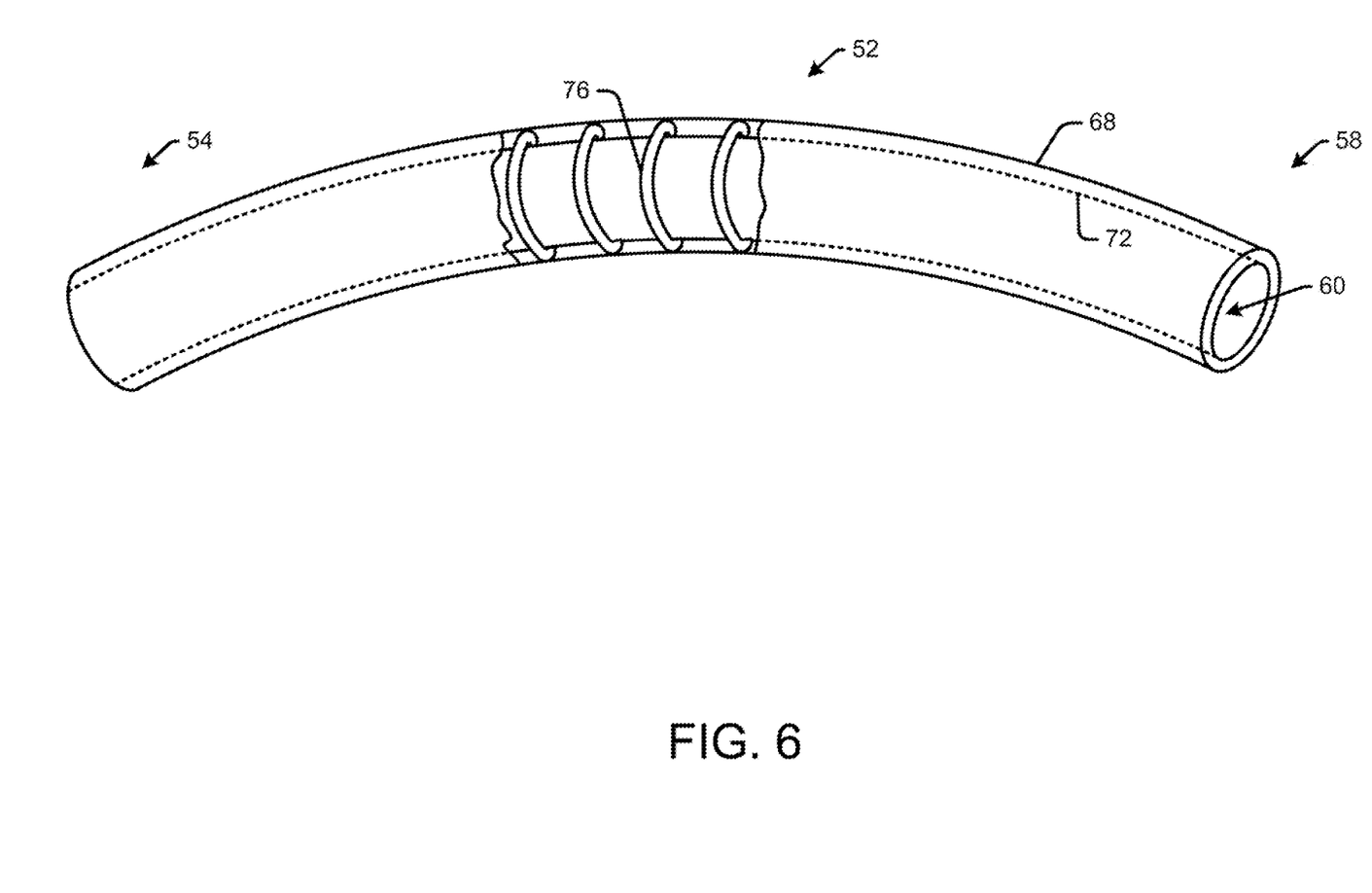
FIG. 6 schematically depicts an example embodiment of a vascular access system.

FIG. 6 depicts the reinforcement member 52 comprising a number of radial projections 76. The radial projections 76 may be spaced apart from one another between the proximal end 54 of the lumen 60 to the distal end 58 of the lumen 60. In some instances, the radial projections 76 is transverse to the length of the lumen 60 or located at another angle relative to the lumen 60. The radial projections 76 may be located at any point between the proximal end 54 of the lumen 60 and the distal end of the lumen 60. The radial projections 76 may include circular protrusions, ribs, struts, etc., or the like. Each of the radial projections 76 may be substantially uniform (such as in a single plane) or curved (such as wave-like). In some instances, the radial projections 76 are positioned between the inner surface 72 and outer surface 68 of the wall defining the lumen 60. In other instances, the radial projections 76 extend radially outward from the outer surface 68 of the wall defining the lumen 60. For example, the radial projections 76 may protrude from the outer surface 68 of the wall defining the lumen 60. In yet other instances, the radial projections 76 extend radially inward from the inner surface 72 of the wall defining the lumen 60. The radial projections 76 may be spaced apart from one another along the axial length of the lumen 60. Any number of radial projections 76 may be used. In embodiments, a device may have as few as 1, 2, 3, 4, 5, 6, 7, 8, 9, 10, or 12 radial projections, as many as 20, 30, 40, 50, 60, 80, or 100 radial projections, or a number of radial projections within a range of any combination of these numbers.

Figure 7:
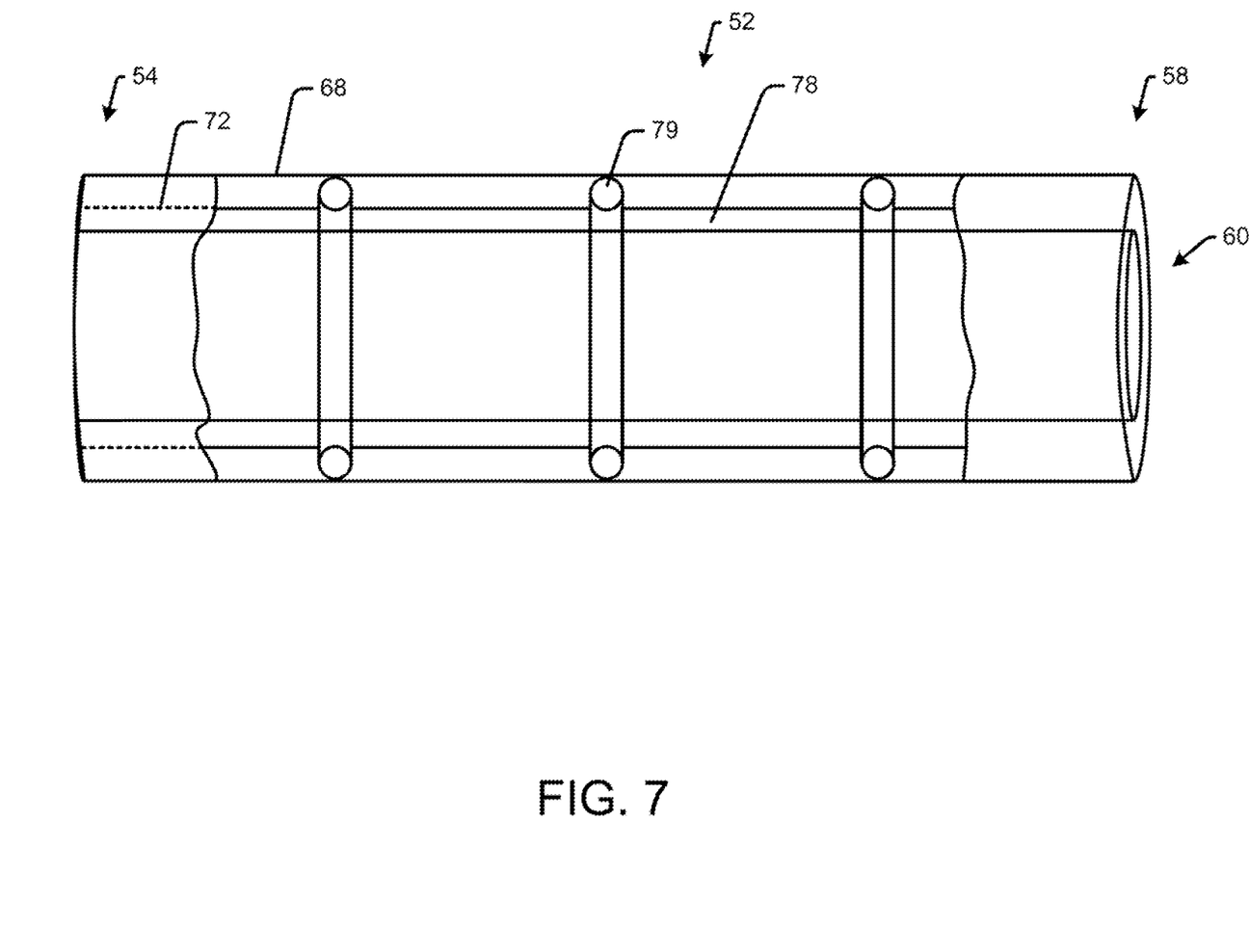
FIG. 7 schematically depicts an example embodiment of a vascular access system.

In certain embodiments, as depicted in FIG. 7, the reinforcement member 52 includes a number of interconnected reinforcement structures (such as tubes or the like). For example, the reinforcement member 52 may include a number of interconnected tubes 78 that collectively extend from the proximal end 54 of the lumen 60 to the distal end 58 of the lumen 60. The interconnected tubes 78 may reinforce the wall defining the lumen 60 while enabling, or at least without substantially impeding, the flexibility of the vascular access system. In some instances, the interconnected tubes 78 extend beyond the proximal end 54 of the lumen 60 and/or the distal end 58 of the lumen 60. In other instances, the interconnected tubes 78 are located at any point between the proximal end 54 of the lumen 60 and the distal end 58 of the lumen 60. The cross section of the interconnected tubes 78 may be any shape, including rectangular, circular, triangular, etc., or the like. In some instances, the interconnected tubes 78 are positioned between the inner surface 72 and the outer surface 68 of the wall defining the lumen 60. In other instances, the interconnected tubes 78 are positioned around the outer surface 68 of the wall defining the lumen 60. In yet other instances, the interconnected tubes 78 are positioned radially inward of the inner surface 72 of the wall defining the lumen 60. The interconnected tubes 78 may be connected by any suitable means 79, including pins, universal joints, pivots, inextensible tethers, cables, etc., or the like. Any suitable number of interconnected tubes 78 may be used.

The reinforcement members 52 also may include interconnected hard segments along a length of the conduit. For example, at least a portion of an end of the interconnected hard segments may overlap adjacent hard segments (similar to the shell of an armadillo).

The illustrated embodiments of the reinforcement member 52 are but a few of many envisioned. For example, the reinforcement member 52 may be a braided structure, an intraluminal stent-type structure, a coil structure, a laser cut tube structure, a number of axial and/or radial grooves or channels, a series of linked reinforcement tube structures, a series of interconnected hard segments, a corrugated tube structure, one or more axial projections, one or more radial projections, any combination thereof, or the like. The reinforcement member 52 may be any number and/or type of structure. The reinforcement member 52 may be positioned between the inner surface 72 and the outer surface 68 of the wall defining the lumen 60, about the outer surface 68 of the wall defining the lumen 60, about the inner surface 72 of the wall defining the lumen 60, or a combination thereof.

The configuration of the reinforcement member 52 can be varied along the length and/or the circumference of the lumen 60. For example, one or more different types of reinforcement members 52 may be disposed between or beyond the proximal 54 and distal ends 58 of the lumen 60. In some instances, the flexibility, kink resistance, axial strength, and/or radial strength of the lumen 60 may be varied along the length of the lumen 60 by selectively coupling different reinforcement members 52, such as a braided structure, a cardiac stent-type structure, a coil structure, a laser cut tube structure, a linked reinforcement tube structure, a series of interconnected hard segments, a corrugated tube structure, axial projections, radial projections, no reinforcement structure, or the like. For example, the reinforcement member 52 may be varied or the characteristics of the reinforcement member 52 may be varied (such as, for example, a pic count of a braided structure) along the length and/or the circumference of the lumen 60. In some instances, certain portions of the lumen 60 do not include a reinforcement member 52, or the reinforcement members 52 cover only one or more subsections of the lumen 60.

Figure 8:
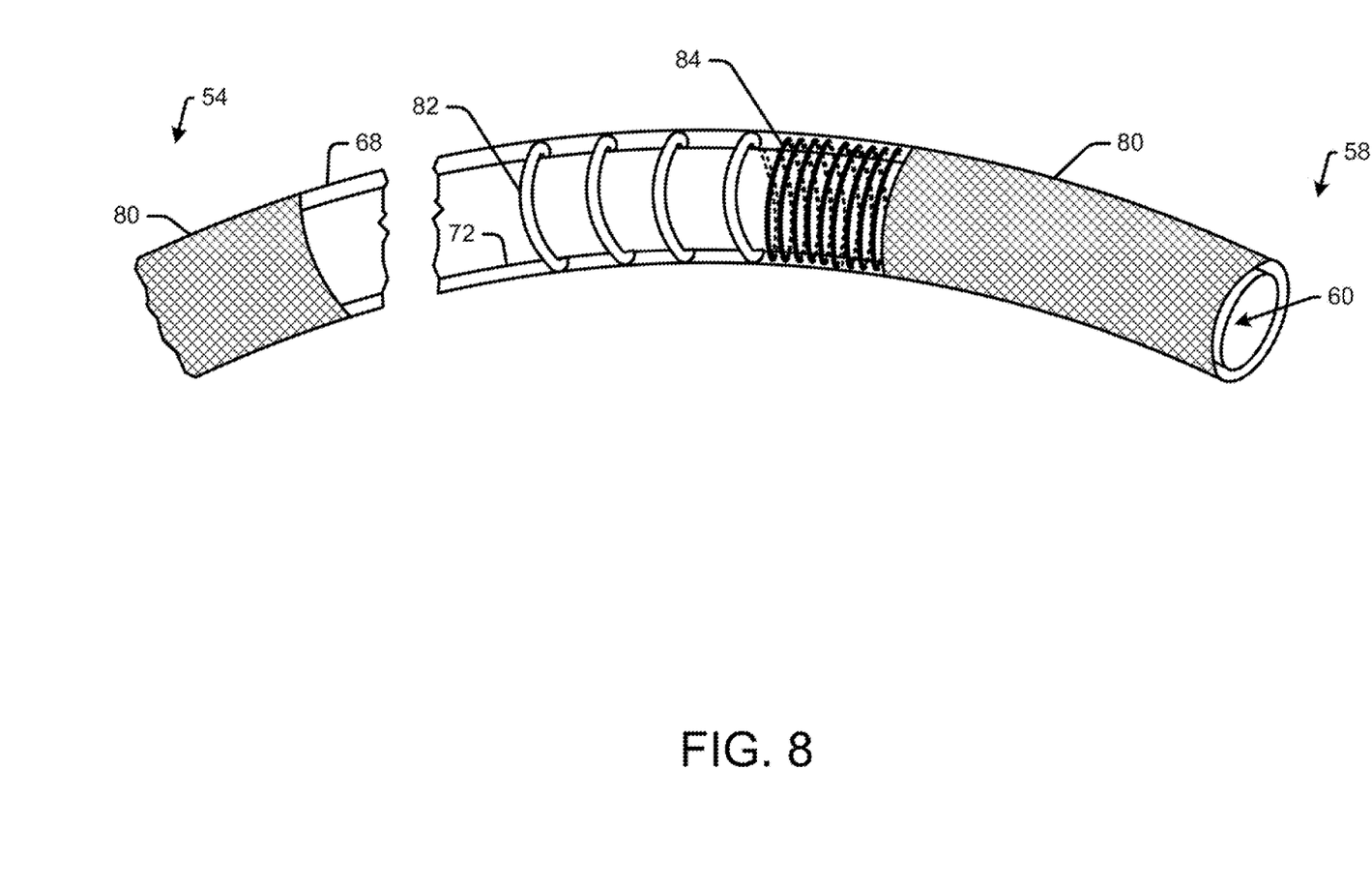
FIG. 8 schematically depicts an example embodiment of a vascular access system.

In embodiments, it may be particularly advantageous to include a combination of two or more different types and/or regional positions of the reinforcement members. For example, one type of reinforcement member may be positioned about a distal end of the lumen and a second type of reinforcement member may be positioned about the proximal end of the lumen. The type and characteristics of the reinforcement members may vary depending on their location. FIG. 8 depicts the lumen 60 defined by a wall structure that includes three different reinforcement members: a first reinforcement member 80, a second reinforcement member 82, and a third reinforcement member 84. Additional or fewer reinforcement members may be used in other embodiments. In some instances, the first reinforcement member 80, the second reinforcement member 82, and the third reinforcement member 84 are different types of reinforcement members. In other instances, the first reinforcement member 80, the second reinforcement member 82, and the third reinforcement member 84 are the same type of reinforcement member. The various reinforcement members 52 may be positioned in any arrangement about the lumen 60. For example, the various reinforcement members 52 may be spaced apart from one another or positioned adjacent to one another. Moreover, in some instances, at least a portion of the wall defining the lumen 60 includes no reinforcement member. For example, a portion of the lumen 60 between the first reinforcement member 80 and the second reinforcement member 82 has no reinforcement member.

The first reinforcement member 80, the second reinforcement member 82, and the third reinforcement member 84 may be positioned between the inner surface 72 and outer surface 68 of the wall defining the lumen 60, about the outer surface 68 of the wall defining the lumen 60, about the inner surface 72 of the wall defining the lumen 60, or a combination thereof. In some instances, the first reinforcement member 80, the second reinforcement member 82, and/or the third reinforcement member 84 extend partially (e.g., from 40% to 99%) or completely about the circumference of the lumen 60.

Combing various types of reinforcement members may enhance ease of use (implant or explant) while particular sections of the conduit are configured to maximize one mechanical property (such as rigidity, flexibility, kink resistant, etc.) over another.

The foregoing vascular access system can be included within a broader method of applying such a device to a patient. Such a method can involve accessing a vein in the patient into which an outflow component is to be inserted. For example, a jugular vein may be accessed in such a method. The distal end of the outflow component can be positioned distant from the access site, e.g., at any location between the access site to a chamber of the heart.

The broader method can also include coupling the proximal end of an inflow component with a vascular segment different from the insertion site, which can be a jugular vein. The inflow component can be coupled with a different vascular segment, e.g., a brachial artery, by any suitable technique. One technique involves suturing the proximal end to the artery, for example producing an end-to-side anastomosis. Attachment of the proximal end of the inflow component can be performed through a second incision formed through the skin adjacent to the vascular segment to which the inflow component is to be connected.

The foregoing devices and variants thereof enable the provision of a vascular access system. The inflow component can be attached by any means to an artery by suturing or otherwise arterialized. In other embodiments, the proximal end of the inflow component can be attached by an expandable member, which can be self-expanding or balloon expandable. A self-expanding version can include a sinusoidal circumferential member adapted to be enlarged to at least the inner size of the artery. This enlargement enables a proximal portion of the inflow conduit to expand toward the inner wall of the artery, e.g., to be pressed into engagement with an internal segment of an artery. Another technique for arterializing the inflow component involves providing a coupling structure, which can be one or more stent-like structures, such as those described for example in U.S. Application Publication No. 2009/0076587, which is incorporated by reference herein in pertinent part. For example, at least a portion of the inflow component, e.g., including at least a portion of the coupling structure, can be deployed within the vessel and the remainder of the inflow component can extend from the vessel to the outflow component.

In one embodiment, a portion of the outflow component is adapted to be inserted within a vein at an insertion site. The outflow component can have an outside diameter which is less than an inner diameter of the vein and can have at least one opening in an end thereof with at least one of the openings in the catheter section to be disposed distant from the insertion site. For example, an outlet can be within a lumen or a chamber of the heart.

In operation, blood flows from the artery through the inflow component and is returned to the venous side of the circulatory system through an opening in the outflow component. The system preferably provides laminar blood flow between the artery and the vein. In certain applications, blood flows through the vein uninterrupted around at least an outer portion of the outflow component.

Access to the system can be provided in any suitable way, such as by providing a needle having a first end coupled to a hemodialysis device and having a second end adapted for insertion directly into the inflow component. Blood may thereby be shunted from the vascular access device to a dialysis device and back to the patient's circulatory system.

Although disclosed in the context of certain preferred embodiments and examples, it will be understood by those skilled in the art that the present disclosure extends beyond the specifically disclosed embodiments to other alternative embodiments and/or uses of and obvious modifications and equivalents thereof. In addition, while several variations have been shown and described in detail, other modifications, which are within the scope of these disclosures, will be readily apparent to those of skill in the art. It is also contemplated that various combinations or sub-combinations of the specific features and aspects of the embodiments may be made and still fall within the scope of the disclosures. It should be understood that various features and aspects of the disclosed embodiments can be combined with or substituted for one another in order to form varying modes of the disclosed embodiments. Thus, it is intended that the scope of at least some of the present embodiments herein disclosed should not be limited by the particular disclosed embodiments described above.

We claim:

1. A system for providing a continuous flow of blood between two locations in a cardiovascular system of a patient, comprising:
a blood conduit configured to be entirely implanted within a patient, the blood conduit comprising:
a conduit wall defining an inner surface and an outer surface,
a proximal portion configured to be attached to an artery, the proximal portion comprising a first material, and
a distal portion configured to be inserted into a blood vessel at an insertion site and to be advanced therethrough to a location spaced apart from the insertion site, the distal portion comprising a second material, wherein the second material is different from the first material; and
a plurality of reinforcement members positioned at least partially about the blood conduit in at least one of the distal portion, the proximal portion, or a combination thereof,
wherein at least one of the plurality of reinforcement members is embedded between the inner surface and the outer surface of the conduit wall, and
wherein at least one of the plurality of reinforcement members is only disposed about a partial circumference of the blood conduit along a portion of the blood conduit,
wherein each reinforcement member of the plurality of reinforcement members comprises one of: a corrugated tube structure, axial projections disposed parallel to a longitudinal axis of the lumen, and axial or radial channels, and
wherein the proximal portion comprises a region configured for repeated needle access.

2. The system of claim 1, further comprising a connector configured to couple the distal portion to the proximal portion.

3. The system of claim 1, wherein at least one of the plurality of reinforcement members is positioned about an inner surface of the blood conduit.

4. The system of claim 1, wherein at least one of the plurality of reinforcement members is positioned about an outer surface of the blood conduit.

5. The system of claim 1, wherein at least one of the plurality of reinforcement members extends to a distal end of the blood conduit.

6. The system of claim 1, wherein at least one of the plurality of reinforcement members extends to a proximal end of the blood conduit.

7. A system for providing a continuous flow of blood between a first vascular segment and a second vascular segment in a cardiovascular system of a patient, the system comprising:
an inflow component comprising a first material and an outflow component comprising a second material, which together define a lumen therethrough,
wherein the second material is different from the first material,
wherein the inflow component is configured to be sutured to the first vascular segment, and
wherein the outflow component is configured to be inserted into the second vascular segment,
whereby continuous flow is provided through the lumen between the first vascular segment and the second vascular segment, and
wherein at least a portion of the lumen comprises a lumen wall defining an inner surface and an outer surface; and
a first reinforcement member, a second reinforcement member, and a third reinforcement member positioned at least partially about the lumen in at least one of the inflow component, the outflow component, or a combination thereof,
wherein each reinforcement member comprises one or more of the following types of reinforcement members: a corrugated tube structure, axial projections disposed parallel to a longitudinal axis of the lumen, axial or radial channels, or a combination thereof,
wherein at least one reinforcement member is embedded between the inner surface and the outer surface of the lumen wall, and
wherein each reinforcement member is configured to maximize a different mechanical property than the other reinforcement members.

8. The system of claim 7, further comprising a connector configured to couple the inflow component to the outflow component.

9. The system of claim 7, wherein at least two reinforcement members are positioned between an inner surface and an outer surface of a wall of the inflow and/or outflow components defining the lumen.

10. The system of claim 7, wherein at least one reinforcement member is positioned about an inner surface of the wall.

11. The system of claim 7, wherein at least one reinforcement member is positioned about an outer surface of the wall.

12. The system of claim 7, wherein the at least one reinforcement member extends to a distal end of the lumen.

13. The system of claim 7, wherein the at least one reinforcement member extends to a proximal end of the lumen.

14. A blood conduit for fluidly coupling a first vascular segment to a second vascular segment, the blood conduit comprising:
a conduit wall defining an inner surface and an outer surface,
a first conduit configured to be attached to the first vascular segment, the first conduit comprising a first material;
a second conduit configured to be attached to the second vascular segment, the second conduit comprising a second material different from the first material,
wherein the blood conduit is configured to be entirely implanted within a patient, and whereby continuous flow is provided through a lumen between the first vascular segment and the second vascular segment; and
a plurality of reinforcement members positioned at least partially about at least one of the first conduit and the second conduit,
wherein each of the plurality of reinforcement members comprises one or more of the following types of reinforcement members: a corrugated tube structure, axial projections disposed parallel to a longitudinal axis of the lumen, axial or radial channels, or a combination thereof, and wherein at least two of the plurality of reinforcement members are embedded between the inner surface and the outer surface of the conduit wall, and wherein the first conduit is configured for attachment to an artery.

15. The blood conduit of claim 14, further comprising a connector configured to couple the first conduit to the second conduit.

16. The blood conduit of claim 14, wherein the plurality of reinforcement members comprises reinforcement members positioned at two or more discrete locations about the first conduit, the second conduit, or a combination thereof.

17. A method for providing a continuous flow of blood between two locations in a cardiovascular system of a patient, the method comprising:

attaching a proximal portion of a blood conduit to an artery, the proximal portion comprising a first material;

inserting a distal portion of the blood conduit into a blood vessel at an insertion site and to be advanced therethrough to a location spaced apart from the insertion site, the distal portion comprising a second material different from the first material; and implanting the blood conduit within a patient, wherein the blood conduit comprises at least two reinforcement members at least partially embedded between an inner surface and an outer surface of a wall of the blood conduit, and wherein the blood conduit further comprises at least one of the following types of reinforcement members: a corrugated tube structure, axial projections disposed parallel to a longitudinal axis of the blood conduit, axial or radial channels, or a combination thereof.

18. The system of claim 7, wherein the first reinforcement member, the second reinforcement member, and the third reinforcement member are positioned at least partially about the lumen in at least one of the inflow component and the outflow component.

* * * * *